United States Patent [19]
Nathel et al.

[11] Patent Number: 6,015,969
[45] Date of Patent: Jan. 18, 2000

[54] MULTIPLE-WAVELENGTH SPECTROSCOPIC QUANTITATION OF LIGHT-ABSORBING SPECIES IN SCATTERING MEDIA

[75] Inventors: Howard Nathel, Albany; Harry E. Cartland; Billy W. Colston, Jr., both of Livermore; Matthew J. Everett, Pleasanton; Jeffery N. Roe, San Ramon, all of Calif.

[73] Assignee: The Regents of the University of California, Oakland, Calif.

[21] Appl. No.: 09/008,234

[22] Filed: Jan. 16, 1998

Related U.S. Application Data

[63] Continuation-in-part of application No. 08/714,745, Sep. 16, 1996, abandoned.

[51] Int. Cl.[7] ................................................ G01B 9/02
[52] U.S. Cl. ........................ 250/227.27; 250/339.12; 356/345
[58] Field of Search .................... 250/227.27, 227.19, 250/221, 339.12, 339.09, 339.07, 340, 341.5; 356/345, 357, 360

[56] References Cited

U.S. PATENT DOCUMENTS 5,459,570  10/1995  Swanson et al. ...................... 356/345

*Primary Examiner*—Edward P. Westin
*Assistant Examiner*—Kevin Pyo
*Attorney, Agent, or Firm*—L. E. Carnahan

[57] ABSTRACT

An oxygen concentration measurement system for blood hemoglobin comprises a multiple-wavelength low-coherence optical light source that is coupled by single mode fibers through a splitter and combiner and focused on both a target tissue sample and a reference mirror. Reflections from both the reference mirror and from the depths of the target tissue sample are carried back and mixed to produce interference fringes in the splitter and combiner. The reference mirror is set such that the distance traversed in the reference path is the same as the distance traversed into and back from the target tissue sample at some depth in the sample that will provide light attenuation information that is dependent on the oxygen in blood hemoglobin in the target tissue sample. Two wavelengths of light are used to obtain concentrations. The method can be used to measure total hemoglobin concentration $[Hb_{deoxy}+Hb_{oxy}]$ or total blood volume in tissue and in conjunction with oxygen saturation measurements from pulse oximetry can be used to absolutely quantify oxyhemoglobin $[HbO_2]$ in tissue. The apparatus and method provide a general means for absolute quantitation of an absorber dispersed in a highly scattering medium.

16 Claims, 2 Drawing Sheets

MULTIPLE-WAVELENGTH SPECTROSCOPIC QUANTITATION OF LIGHT-ABSORBING SPECIES IN SCATTERING MEDIA

RELATED APPLICATION

This application is a continuation-in-part of U.S. patent application Ser. No. 08/714,745, filed Sep. 16, 1996, now abandoned.

NOTICE OF GOVERNMENT INTEREST

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to quantitative spectroscopy in turbid media or highly scattering media and more particularly to absolute measurements of various blood constituents in living tissue by non-invasive, non-harmful methods.

2. Description of Related Art

Near infrared radiation with wavelengths of 600–1400 nanometers passes easily through living tissue. However, these same wavelengths are variously affected by tissue oxyhemoglobin concentration, e.g., on the basis of hemoglobin absorbance. The overall range is limited in wavelength, e.g., on the long wavelength side of the spectrum, longer than 1400 nanometers, by water absorption, and on the short wavelength side of the spectrum, shorter than 600 nanometers, by blood absorption. Between these higher and lower limits, the light that does penetrate the tissue is highly diffuse due to scattering. Such diffusion can otherwise obscure information that could be extracted from the non-scattered light. See E. M. Sevick et al., "Quantitation of Time- and Frequency-Resolved Optical Spectra for the Determination of Tissue Oxygenation," Analytical Biochemistry 195, pp. 330–351 (1991).

Optical diagnostic systems have been built to take advantage of the near infrared translucence of living tissue, but these prior art systems are seriously handicapped by the photon scatter that occurs within the highly diffuse tissue. One of the earliest used optical techniques, called pulse oximetry, was only able to provide estimates of the oxygen saturation of blood, e.g., by using the phenomenon of differential transmission of light caused by oxyhemoglobin and reduced hemoglobin. Saturated oxygen ($SaO_2$) is defined as the percentage of oxygen bound to hemoglobin compared to the total hemoglobin available for reversible oxygen binding. Unfortunately, with pulse oximetry the absolute concentration of free oxygen in the blood could not be discerned, because it has no NIR signatuare. Only the ratio of oxyhemoglobin to total hemoglobin can be determined through human tissue.

Quantitative spectroscopy through tissue with optical radiation is facilitated by the use of scatter elimination techniques, which fix the photon path length. Measurements of the attenuation due to the material of interest in the medium is difficult without a means to discriminate the non-scattered-photons from the scattered-photons, because the amount of medium involved (i.e. pathlength) is indeterminate. In useful applications, the exact path lengths must be determined for sub-surface light penetrations of tissue that range up to several millimeters.

Time-domain and frequency-domain methods can be used for the discrimination of light that has undergone considerable scattering to selectively detect the non-scattered, first arriving photons. Scattered photons necessarily travel over longer distances and take more uncertain pathways than do ballistic or quasi-coherent photons. The non-scattered photons traverse much shorter path lengths and exit the medium in a small, forward cone. The best quantitative information is carried in the photons that are relatively non-scattered, and these arrive first at the detector from the medium. Time-resolved techniques have conventionally been used to discriminate between scattered and non-scattered light exiting tissues based on time-of-flight. Optical coherence techniques rely on the short coherence length of a broadband low-coherence light source to provide time-of-flight information interferometrically via autocorrelations. Measurements are therefore restricted to relatively non-scattered, first arriving (i.e. ballistic) photons.

Time domain techniques, such as streak cameras, require sub-picosecond laser systems which are expensive, non-compact, and complicated. Frequency-domain techniques, however, use inexpensive optical sources, optical low-coherence reflectometry (OLCR), and avoid the need for complicated systems. State-of-the-art reflectometers use diode light sources and fiberoptics that make for compact and modular systems that are capable of micrometer spatial resolutions and high detection sensitivities.

The relative transparency of biological tissues to near infrared (NIR) light allows the absorption properties of intact organs to be monitored non-invasively. The NIR absorption caused by hemoglobin and cytochrome oxidase can be measured and used to monitor changes in blood and tissue oxygenation. Such measurement methods were first applied to the brain of cats and subsequently to the brains of newborn infants and adults. Recently, methods for the absolute quantitation of cerebral blood flow and blood volume have been developed and applied to newborn infants and adults. The possibility of imaging of tissue oxygenation by NIR light has also been studied by various groups.

Quantitative interpretation of spectroscopic data using the Beer-Lambert law requires that the optical pathlength be known, otherwise the light intensity measurement is meaningless because the distance over which it was attenuated is unknown. At best, the prior art only approximates the pathlength. In near infrared spectroscopy (NIRS), light scattering by the tissues prevents detecting all the light that entered the tissues. The source light travels along a distribution of paths. It has, however, previously been shown that a modified Beer-Lambert law can be applied to quantify changes in chromophore concentration from the measured changes in tissue attenuation. This modified law uses the differential pathlength, which is defined as the local gradient of the attenuation versus the absorption coefficient $\mu_a$ of tissue. It has been shown experimentally that the differential pathlength can be approximated by measuring the mean distance L traveled across the tissue by picosecond light pulses or by measuring the phase shift of a frequency modulated light source. The differential pathlength factor which is obtained when the mean pathlength <L> is divided by the distance between light source and detector optrodes, has been shown to be approximately constant once the optrode spacing exceeds 2.5 cm.

To date, the use of differential pathlength factors have only been demonstrated to be valid for homogeneous mediums. But real organs consist of various tissue components that have different optical parameters. Therefore, for accurate quantitation of data, it is important to understand the nature of light transport through an inhomogeneous medium and to know the effective optical pathlengths within the various portions of the medium.

M. Hiraoka discusses various methods for calculating light transport through tissue, in "A Monte Carlo investigation of optical pathlength in inhomogeneous tissue and its application to near-infrared spectroscopy", Phys. Med. Biol. 38, pp. 1859–1876 (1993). One approach is to seek an analytical solution of the diffusion equation. However, this has only succeeded under restricted geometries and for a homogeneous medium. A second approach is the "Monte Carlo" method which can be applied to inhomogeneous media and has the advantage of being able to calculate the pathlength directly. This method keeps track of individual photon histories but requires considerable computation time. A third approach is to solve the diffusion equation numerically by the finite-difference method. This has been successful under restricted conditions for all inhomogeneous media. A fourth approach is to solve the diffusion equation by the finite-element method, which can be applied to the complex geometries of an inhomogeneous medium and has the advantage of fast calculation time. However, it does not calculate individual photon histories.

The lack of accurate pathlength information has therefore complicated an otherwise useful measurement tool.

SUMMARY OF THE INVENTION

An object of the present invention is to provide a method and system for the simple determination of the pathlength of ballistic, non-scattered photons that travel through highly diffuse mediums.

A further object of the present invention is to provide a non-invasive method and system for measuring the oxygen concentrations in blood hemoglobin.

Another object of the present invention is to provide a method and system for multiple-wavelength spectrographic quantitation of light-absorbing species in highly diffuse inhomogeneous mediums.

Briefly, an absolute total hemoglobin (crit) and oxyhemoglobin concentration measurement system of the present invention for blood in tissue comprises multiple short-coherence optical light sources that are coupled by single mode fibers through a splitter and combiner and focused on both a target tissue sample and a reference mirror. Reflections from the reference mirror and light that has passed through the target tissue sample are mixed to produce interference fringes. The reference mirror is set such that the optical distance traversed in the reference path is the same as the optical distance traversed through the target tissue sample that will provide light attenuation information that is dependent on the oxygen in blood hemoglobin in the target tissue sample. Multiple wavelengths of near infrared light can be used to eliminate the uncertainty that would otherwise be included from light scattering in the tissue.

An advantage of the present invention is that a method and system are provided for measuring the concentration of total hemoglobin and oxyhemoglobin in living tissue by non-invasive, harmless means.

Another advantage of the present invention is that a method and system are provided for the simple determination of the pathlength of ballistic, non-scattered photons that travel through highly diffuse mediums.

A still further advantage of the present invention is that a general method and system are provided for multiple-wavelength spectrographic quantitation of light-absorbing species in highly diffuse inhomogeneous mediums.

DETAILED DESCRIPTION OF THE INVENTION

Figure 1:
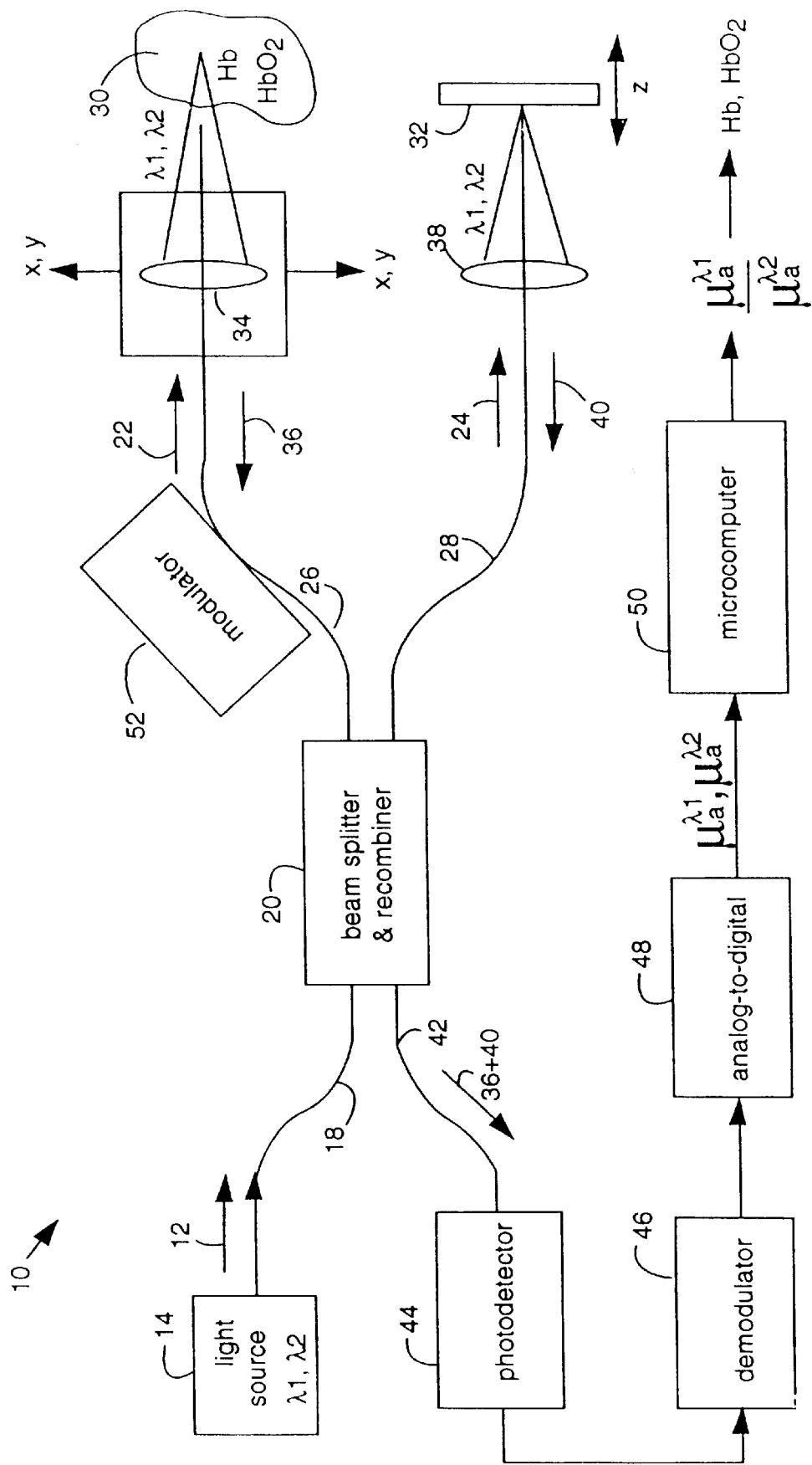
FIG. 1 is a schematic diagram of a reflective-light-sample-measurement system embodiment of the present invention for multiple-wavelength spectrographic quantitation of light-absorbing species in highly diffuse inhomogeneous mediums.

FIG. 1 shows a method and system for multiple-wavelength spectrographic quantitation of light-absorbing species in highly diffuse inhomogeneous mediums in an embodiment of the present invention, referred to herein by the general reference numeral 10. A single-frequency system used to detect dental caries is similarly disclosed by one of the present inventors, Howard Nathel, in a previous U.S. patent application, Ser. No. 08/250,492, filed May 27, 1994, and incorporated herein by reference. In system 10, the objective is the quantitation of two different light-absorbing species, hemoglobin with and without oxygen ($HbO_2$ and Hb), that each respond differently to two or more near infrared wavelengths, for instance, $\lambda_1$ and $\lambda_2$.

The obscuring effects of photons scattered by tissue to reflected-light-amplitude measurements can be largely eliminated by optical coherence interferometry, e.g., optical time domain reflectometry or optical coherence reflectometry. The length of the reflected, non-scattered light path through the tissue medium becomes a trivial matter when using a reference beam. A beam of photons 12 from a multiple wavelength source 14 of non-ionizing radiation, e.g., optical light at $\lambda_1$ and $\lambda_2$, is sent down a single mode fiber 18 to a beam splitter and recombiner 20 where it is split into a sample beam 22 and a reference beam 24. These travel down their respective single mode fibers 26 and 28 toward a tissue sample 30 and a reference mirror 32. The sample beam 22 is focused onto the surface of the tissue sample 30 by a lens 34 that is movable in the x,y plane perpendicular to the surface of the tissue sample 30. The reference beam path contains a mirror 32 which is adjusted longitudinally to vary the measurement depth and it can be used to impart a Doppler shift on the beam. The Doppler modulated reference beam beats against the sample beam at the frequency difference and gives rise to a heterodyne signal.

In a particular application, the concentrations of Hb and $HbO_2$ in the tissue sample 30 are to be determined.

A beam 36 of reflected photons, both scattered and non-scattered, coherent and non-coherent, is collected by the lens 34 and directed back to the beam splitter and recombiner 20. The various constituents of beam 36 have been attenuated in amplitude both by the distance and the material composition of the tissue material through which it has had to pass. Simultaneously, the reference beam 24 is directed by the single mode fiber 28 to be focused on the reference mirror 32 by a lens 38 and reflected back as a beam 40. The mirror 32 is adjustable in the z-direction such that the pathlength that each of beams 24 and 40 must traverse between the beam splitter and recombiner 20 and the reference mirror can be manipulated.

At a point within the beam splitter and recombiner 20, the beam 36 reflected back from the sample 30 and the beam 40 reflected back from the reference mirror 32 will mix. The mixing produces an interference pattern only between the photons that had the same time of flight in the sample path and reference path. The photons in the beam 36 will have experienced a variety of pathlengths and effects to their individual polarization and phase due to the highly diffuse nature of the tissue sample 30. The photons in the beam 40 will have experienced only one sharply defined pathlength and little effect to their individual polarization and phase due to the highly reflective single plane nature of the reference mirror 32. Thus, those photons in the reflected sample beam 36 that are within a coherence length of having traveled the same distance in their respective paths as photons in the reflected reference beam 40 will produce interference fringes. The fringe amplitude is proportional to the square root of the number of selected photons in the reflected sample beam 36. In an inhomogeneous medium such as the tissue sample 30, studies may be conducted for the absorbencies of various species at a variety of depths and with a variety of optical wavelengths. Thus the x,y positionability of the lens 34 may be used to collect data for the tomographic representation of the tissue sample 30 in three-dimensions, plane-by-plane. Each plane of data is collected by a corresponding z-positioning of the reference mirror 32.

Another single mode fiber 42 connects the interference fringe outputs of the beam splitter and recombiner 20 to a photodetector 44 for conversion to an electric analog signal. An interferogram is collected by the photodetector 44 and demodulated and amplified at 46. An analog-to-digital converter (ADC) 48 conditions the signal for input to a microcomputer 50.

Optical heterodyne detection may be used to eliminate background interference caused by the diffusely scattered photons returning from the sample tissue 30. For example, a modulator 52, e.g., a piezoelectric transducer or an acousto-optic modulator, can be inserted in either the sample beam 22 or reference beam 24 to introduce a Doppler shift. The heterodyned signal can be demodulated with an envelope detector (such as a lock-in or log amplifier). Sensitivity that approaches the shot noise limit, or quantum limit, is possible. See, Gilgen, et al., "Sub-millimeter optical reflectivity", J. Lightwave Technol. 7(8):1225–1233 (1989); and, Beaud et al., "Optical reflectometry with micrometer resolution for the investigation of integrated optical devices", IEEE J. Quantum Electron., 25(4):755–759 (1989).

In an alternative embodiment, the reference mirror 32 may be vibrated or simply scanned in the z-direction to produce the Doppler shift for optical heterodyne detection if the sample beam is not modulated using the modulator 52.

The optical light source 14 may be a highly coherent type that is switched to emit pulses of 10—10to 10–14 second duration. For example, mode-locked diode lasers, diode-pumped mode-locked solid-state crystal sources, and diode-pumped mode-locked rare earth-doped fiber laser sources could be used. With a coherent source, time domain interferometry is used to reduce interference from scattered photons. The reference and sample beams are synchronized by adjusting the position of the reflecting mirror so that the maximum number of coherent reflected sample photons contribute to the interference pattern formed by recombining the reference beam with the reflected sample beam. In practice the reflected sample beam will consist of scattered and non-scattered photons; the photons that are scattered by the tissue have a longer path length, and so are not synchronized with the reference beam and do not contribute to the formation of an interference pattern. With a pulsed source, the ultimate resolution of the optical imaging system is related to the pulse width. Millimeter and sub-millimeter resolution requires a source pulse of several picoseconds or less.

At least two wavelengths of light must be used. One such wavelength is chosen to be within an absorption band of the species whose concentration is to be determined. The other wavelength is chosen to be outside such absorption band. Either two sources at different wavelengths, or a single source with a broad bandwidth that spans the absorbing and non-absorbing spectral space can be used. The reference wavelength is used to normalize for scattering losses at the on-resonance wavelength. In this way losses due only to scattering can be accounted for.

The attenuation of light over a known path length, L, provides a quantitative description of the concentration of light absorbing species via the Beer-Lambert relationship, $$\mu_a = -\frac{1}{L}\log_e \frac{I}{I_0} = \varepsilon\,[C],$$

where e is the extinction coefficient ($cm^{-1}$ $mM^{-1}$), [C] is the concentration of absorber (mM), I and $I_0$ are the detected and incident light intensity, and $\mu_a$ is the absorption coefficient of the sample in units of $cm^{-1}$. Thus with L determined by fixing the detected photons to a straight line-of-sight (not scattered), I and I0 measured, and $\epsilon$ known as a function of wavelength, the concentration of the absorber of interest can be determined.

The light source 14 in the preferred embodiment is a continuous-wave low-coherence, or broadband, source. Preferred low-coherence sources include super-luminescent diodes, diode-pumped solid state crystal sources, and diode-pumped rare earth-doped fiber sources. An interference pattern is formed only when the sample and reference pathlengths are equal to within the source coherence length, which is inversely proportional to the source bandwidth. Photons in the sample beam that are scattered within the tissue are asynchronous and incoherent with the photons in the reference beam, and therefore do not contribute to the interference pattern formed by combining the reflected reference beam and the reflected sample beam.

The path length information can be obtained directly for quantitation. Either time-domain or frequency-domain interferometry is used for such isolation. A reflection optical coherence spectroscopic quantitation system can also be used in a time-domain mode, e.g., based on a Michelson interferometer, which uses a short pulse, $10^{-14}$ to $10^{-10}$ seconds, light source. Interference fringes occur when the light from a reference arm is synchronized to straight back-scattered light from a sample. Diffusely back-scattered light is therefore asynchronous with the reference arm pulse and only straight back-scattered photons will interfere with the reference pulse. In this way exact path length of the light traversing the samples is known and therefore quantitative information can be ascertained.

By effectively selecting only the light that contributes to the interferometric signal, the corresponding path lengths can be determined and/or fixed for the multiple-wavelength measurements. Interference fringes will occur when using broadband, low-coherence light sources only when the sample and reference path lengths are within a source coherence length. (The source-coherence length is inversely proportional to bandwidth.) The diffusely back-scattered light from the sample is beyond the coherence length of the source. In this way the pathlength of detected photons are fixed to those of only straight back-scattered photons. Further scatter reduction takes place because interference only occurs between photons of the same polarization state. Scatter tends to depolarize the light from the sample. Signals are recorded as interferograms, e.g., optical heterodyne detection records. The signals are processed electronically to yield an amplitude value for the non-scattered light. Passive optical heterodyne detection can be done by using a scanning mirror to impart a Doppler shift on the light signal. Active optical heterodyne detection can be done by placing a piezoelectric or acousto-optic modulator in the reference or signal arm. Scatter discrimination techniques are similar to range-gating techniques used to image through turbid media, e.g., fog or water. The photons that undergo minimal, or no scattering, are discriminated from highly-scattered photons.

In another embodiment of this invention where straight through (not backscattered) photons are detected, a Mach-Zehnder interferometer configuration would be used, e.g., as in U.S. patent application, Ser. No. 08/250,492, filed May 27, 1994.

How powerful the light source needs to be for such a system depends on the application, the optics used, and the distances needed to be traversed through the turbid media. For medical applications, power is limited by ANSI burn standards. Compact, low power, broadband sources include super-luminescent diodes, diode pumped Yb or Nd doped glass fiber luminescent sources, and diode pumped solid-state (such as Cr:forsterite, Cr:LiSAF or Cr:LiCAF) amplified spontaneous emission (ASE) sources. Mode-locked lasers can be used for compact, higher power, short pulse sources.

Figure 2:
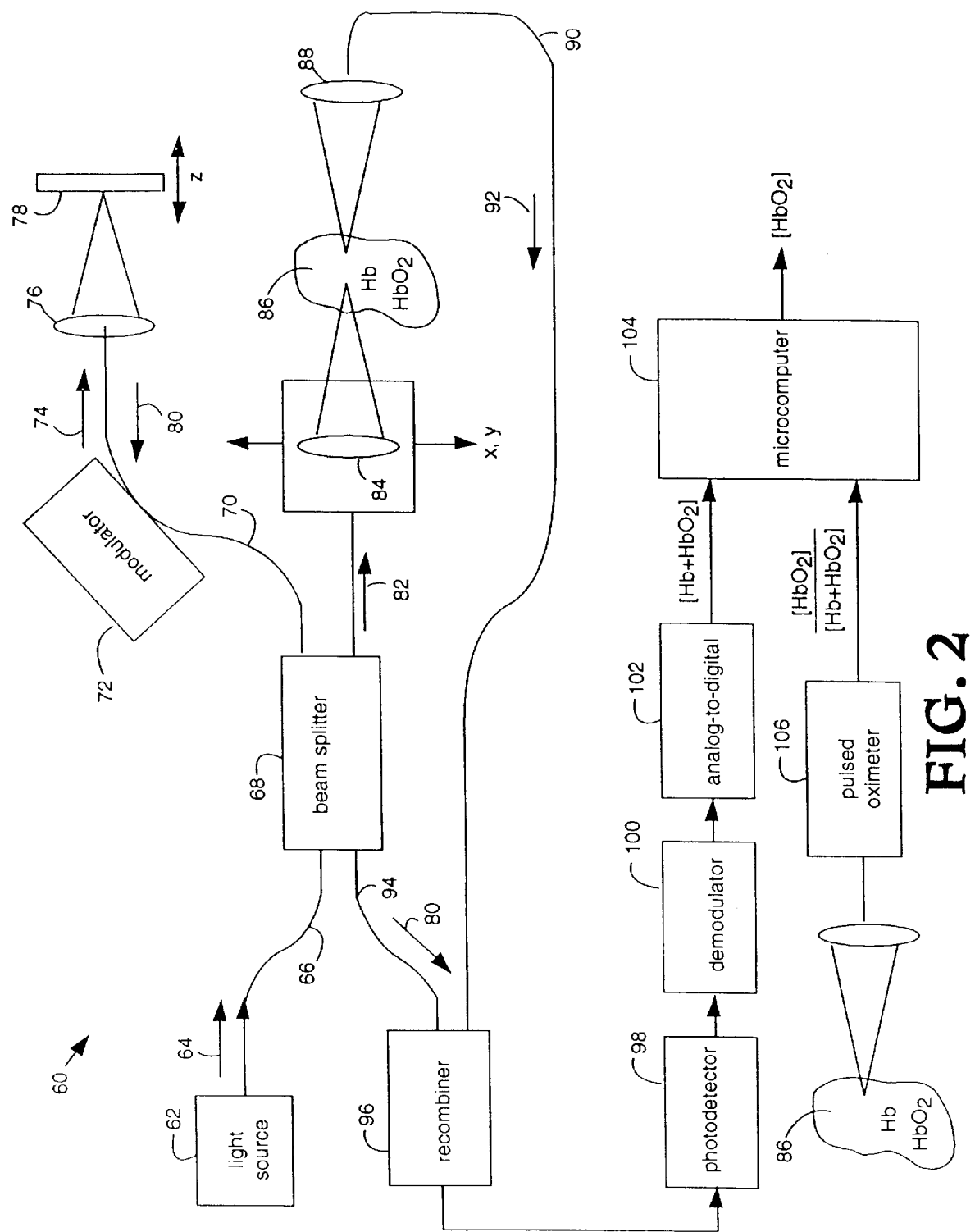
FIG. 2 is a schematic diagram of a transmissive-light-sample-measurement system embodiment of the present invention, similar to that of FIG. 1, for finding total hemoglobin in a sample tissue, but further including a pulsed oximeter for finding the ratio of oxygenated blood hemoglobin to total hemoglobin, and a microcomputer to compute from these two determinations the oxygenated blood hemoglobin.

FIG. 2 is a schematic diagram of a transmissive-light-sample-measurement system embodiment of the present invention, referred to herein by the general reference numeral 60. The system 60 is similar to system 10 of FIG. 1. Both are useful for finding the total hemoglobin in a sample tissue. Two very different modes of operation may be used, e.g., a first employing a pulsed source 62 and a second employing a low coherence continuous wave source. A source light 64 is carried down a fiberoptic cable 66 to a beam splitter 68. A second fiber optic cable 70 connects to a modulator 72. A first split beam 74 is carried to a lens 76 focused on a target reference mirror 78 that is adjustable in the z-axis, e.g., in and away from the lens 76 decreasing and increasing the path length of a reflected beam 80. A second split beam 82 is focused by a lens 84 to pass through a sample 86, e.g., a tissue with blood hemoglobin, to another lens 88 and a fiberoptic cable 90. The lenses 84 and 88 can be adjusted in both the x-axis and y-axis to change the path taken through sample 86. A transmissive light sample 92 and the reflected beam 80 from a fiberoptic cable 94 are combined in a recombiner 96. The reflective sample light system described in FIG. 1 is an alternative approach. Here, light having the same optical path length will interfere and setup fringe patterns that can be amplitude detected by a photodetector 98, and so is similar to system 10. A demodulator 100 removes any modulation injected by the modulator 72. An analog-to-digital converter 102 essentially provides the measurement information needed by a microcomputer 104 to determine the total hemoglobin [Hb+HbO$_2$] in the sample 86. A conventional pulse oximeter 106 is used for finding the ratio of oxygenated blood hemoglobin to total hemoglobin [HbO$_2$/(Hb+HbO$_2$)]. The microcomputer 104 is programmed with software to compute from these two determinations the oxygenated blood hemoglobin, e.g., given [Hb+HbO$_2$] and the ratio [HbO$_2$/(Hb+HbO$_2$)], it finds [HbO$_2$].

In general, the amplitude of collected light at each wavelength must be independently measured to determine the appropriate ratios. Artisans will be aware of several conventional ways that are well-known to separate the individual wavelengths and measure their amplitudes. In addition to measuring amplitude, a heterodyne method of the present invention measures the phase of the returning light as a function of wavelength. Since absorption strongly affects the phase velocity of light, it is possible to determine the absorption coefficient at various wavelengths based on the wavelength dependence of the phase of the returning light. The phase velocity of light versus wavelength, also known as group velocity dispersion, is in itself a useful measurement.

In an alternative embodiment of the present invention, the detection of each returning wavelength of light can include separating the different wavelengths using dichroic optics, gratings, fiber optic wavelength division multiplexing, etc., and then sending each wavelength to a different detector to be measured.

In a further embodiment of the present invention, all the return light is measured by the same detector, and the amplitude at each wavelength is determined by signal processing. The heterodyne frequency associated with the Doppler shift is inversely proportional to the wavelength of light being measured. The reflected amplitude of each wavelength can be measured separately by selecting the appropriate heterodyne frequencies with bandpass filters or lock-in amplifiers.

In a still further embodiment of the present invention, all the return light is measured by the same detector. The spectral amplitude and/or phase of the reflected light, as a continuous function of wavelength, is determined using a Fourier transform of the heterodyned signal. The absorbancy-versus-wavelength of the sample media can be determined by the spectral amplitude of the reflected light, the phase versus wavelength of the reflected light, or both.

The phase velocity of light versus wavelength of the sample can also be determined by the spectral phase versus wavelength of the reflected light.

Transepidermal water loss (TEWL) is a measurement of the total amount of water vapor that passes through the stratum corneum by passive diffusion that is not attributed to sweating. Measurements of TEWL have been used to assess the local effects of drugs, occlusive materials, and other substances applied to the skin. Predictive irritancy tests are used either to select the least irritating substance from a variety of substances (such as soaps, solvents, moisturizers, etc.) or to select a population at risk for chronic irritant contact dermatitis. The TEWL measurement at local skin sites is also used by many research centers to evaluate the water-barrier function of both normal and diseased skin in both neonates and adults. The barrier function is disturbed, for example, in dermatitis, ichthyosis, and psoriasis. TEWL measurements are particularly useful in cases where clinically normal looking skin is functionally abnormal, as in the case of noneczematous atopia. Finally, the recovery processes of wound healing have been evaluated by monitoring water loss at the injured site. A wide variety of techniques have been developed for measuring the stratum corneum water content, including electrical measurements, microwave propagation, heat conductivity, photoacoustic spectroscopy, viscoelastic properties, friction, dye fluorescence, and topography. These techniques are, unfortunately, characterized by poor quantitative resolution or inadequate penetration depth. Conventional near infrared spectroscopy, in particular, is limited in a highly scattering media such as tissue since the pathlength of any single photon entering the tissue is determined by the number of scattering events it undergoes. Since this quantity is not measurable, it is subsequently difficult to discriminate between the amount of light lost from scattering and that due to absorption. The use of optical coherence quantitation (OCQ) selectively gates out the scattered component. Water is an ideal target for the use of optical measurement techniques since it has relatively large absorption peaks in the near infrared portion of the EM spectrum and is present in large quantities in the skin.

Only the most strongly absorbing species with little interfering absorption overlap from other chemicals can be measured with only two wavelengths. Water and hemoglobin are two species that can be measured with only two wavelengths, but three or more wavelengths can improve the accuracy and precision of even these measurements. There are many more chemicals that need more than two wavelengths to make a measurement in the concentration range required because the total sample composition has other interfering absorption bands.

The present invention includes quantitation of other light-absorbing and light-scattering species using multiple wavelengths, since scattering can also be quantitated.

Absorption can be determined in thin layers throughout the sample volume so that regional absorbance can be mapped out. Useful applications in skin research and industry therefore exist in the realm of the present invention. For example, skin analysis for burn victims or skin disease diagnostics require a knowledge of the thickness of melanin layer and the location of blood supply. The skin blood supply is primarily made up of two mats called the superficial vascular plexus 0.5 mm below the skin and the vascular plexus located 4–5 mm below the skin. They are both located parallel to the skin and supplied by large feeder vessels from deeper in the body. Knowing the location of these layers would allow more accurate diagnosis and better treatment in a variety of skin problems.

For basic and clinical skin research, chemical measurements are best be done on living tissue. Biomedical researchers require a diagnostic technology that allows noninvasive chemical measurement in living tissue leading to the investigation of dynamic processes in tissue as a function of space and time. Applications include tissue regeneration and wound healing, microcirculation, delivery and distribution of metabolic analytes and drugs, and the characterization of skin disease states.

There are outstanding advantages to being able to study living skin in real time without violating its boundaries by surgery or other interventions. OCT makes it possible to characterize the biochemical, cytologic, anatomic and physiologic features of skin in health and disease. This OCT technique will make it possible to determine quantitatively specific tissue components such as melanin, hemoglobin, elastin, etc., in sharply focused twenty millimeter sections of living skin from the surface through the dermas in real time with no disturbance to the tissue. Layer by layer, a chemical picture of the health of the skin can be obtained. One example is the diagnosis and treatment of malignant melanoma. With this technique, not only will the contours of the tumor be visualized, but the mitotic rate, degree of anaplasia, infiltration of cells beyond the tumor margin, antigenic markers and other attributes could be measured to help in planning for surgery. Another use would be in determining the treatment regimen for psoriasis. Clinical assessment of when the lesions have cleared is not enough because the skin can appear healthy, but histologic studies have shown that beneath the stratum corneum layer the lesional skin can remain abnormal for many weeks, even months. Knowledge of the disease state would allow continued treatment, and no relapses at the site.

A system that could monitor absorption versus depth would also be helpful in industry for determining mixing and drying efficiency. Accurate and precise concentration measurements in turbid media are necessary in many industrial on-line process control schemes. Today's most popular on-line measurement systems use reflective light absorption to determine critical ingredient concentrations. Unfortunately, this technology can not differentiate a scatter change from an absorption change, and this reduces both the accuracy and precision of the concentration measurement.

The on-line monitoring of an active ingredient in a scattering matrix is important in adding the active ingredients in pharmaceutical tablets and cosmetic sun screen products, controlling the dye concentration in paint, and measuring the water content in medical chemistry strips, foods, grains, and lumber.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. A multiple-frequency spectroscopic quantitation method for measuring light-absorbing species in turbid inhomogeneous mediums, the method comprising:

generating a light beam having two different wavelengths of light;

the generating of said two different wavelengths of light being such that one wavelength is selected not to be absorbed by a particular one of the individual targeted species and the other wavelength is selected to be strongly absorbed by the particular one of the individual targeted species, optically splitting said light beam into a sample beam and a reference beam;

passing said sample beam through a sample comprised of a turbid inhomogeneous medium that is host to a plurality of individual targeted species;

optically collecting said sample beam affected by said turbid inhomogeneous medium into a reflected sample beam;

reflecting said reference beam on a variable distance mirror with a highly reflective surface;

optically collecting reflections of said reference beam from said mirror into a reflected reference beam;

optically mixing said affected sample beam and said reflected reference beam, wherein those photons in the affected sample beam that are within a coherence length of having traveled the same distance in their respective pathlengths as those photons in the reflected reference beam provide for interference fringes for each of said two different wavelengths of light that have an amplitude proportional to the square root of the number of selected photons in the reflected sample beam;

detecting and demodulating the amplitudes of said interference fringes for each of said two different wavelengths of light and providing an electric signal proportional to each of said interference fringe amplitudes; and ratioing said proportional electrical signals and relating a ratio derived therefrom to a concentration of said individual targeted species in said turbid inhomogeneous medium.

2. The method of claim 1, wherein:

the generating of said light beam includes producing at least two different wavelengths, $\lambda_1$ and $\lambda_2$, of light selected for their particular light absorbance characteristics by individual targeted species and directing both wavelengths of light into a light beam.

3. The method of claim 1, wherein:

the generating of said light beam includes producing a resultant beam from combining light from at least two sources operating at different wavelengths of light selected for their particular light absorbance characteristics by individual targeted species.

4. The method of claim 1, wherein:

the generating of said light beam includes producing a light beam from a single source with a spectrum of wavelengths of light selected according to particular light absorbance characteristics of an individual targeted species.

5. The method of claim 1, further comprising:

detecting each returning wavelength of light by separating different wavelengths and sending each such separated wavelength to a different detector to be measured.

6. The method of claim 2, wherein:

the difference measured between the ratios of the amplitudes of the collected signal (in dB) to the incident signal corresponding to said interference fringes for each of said two different wavelengths of light represents an absolute measure of the concentration of that particular one of the individual targeted species according to the Beer-Lambert Law.

7. The method of claim 1, wherein:

the generating of said light beam includes the use of at least one of light pulses for time-domain mode and continuous wave light for frequency-domain mode of operation.

8. A multiple-frequency spectroscopic quantitation method for measuring light-absorbing species in turbid inhomogeneous medium, the method comprising:

generating a light beam;

optically splitting said light beam into a sample beam and a reference beam;

passing said sample beam through a sample comprised of a turbid inhomogeneous medium that is host to a plurality of individual targeted species;

optically collecting said sample beam affected by said turbid inhomogeneous medium into a reflected sample beam;

reflecting said reference beam on a variable distance mirror with a highly reflective surface;

optically collecting reflections of said reference beam from said mirror into a reflected reference beam;

optically mixing said affected sample beam and said reflected reference beam wherein those photons in the affected sample beam that are within a coherence length of having traveled the same distance in their respective path lengths as those photons in the reflected reference beam provide for interference fringes for each of said two different wavelengths of light that have an amplitude proportional to the square root of the number of selected photons in the reflected sample beam;

detecting and demodulating the amplitudes of said interference fringes for each of said two different wavelengths of light and providing an electric signal proportional to each of said interference fringe amplitudes;

ratioing said proportional electrical signals and relating a ratio derived therefrom to a concentration of said individual targeted species in said turbid inhomogeneous medium;

determining the total tissue concentrations of oxy and deoxygenated forms of hemoglobin $HbO_2$ and $Hb$ from the step of ratioing;

using pulse oximetry to determine the hemoglobin saturation ratio $SaO_2 = HbO_2/(Hb+HbO_2)$ in said sample; and computing the absolute level of oxygenated blood hemoglobin from said total tissue concentrations of oxy and deoxygenated forms of hemoglobin $HbO_2$ and $Hb$ and said hemoglobin saturation ratio $SaO_2 = HbO_2/(Hb+HbO_2)$ in said sample.

9. The method of claim 1, further comprising the step of:

Doppler shifting at least one of the sample beam and reference beam to introduce beating of the reference and sample signals and thus allow for optical heterodyne detection.

10. The method of claim 9, further comprising the step of:

measuring all the return light with a single detector and using signal processing to determine the amplitude of light at particular wavelengths;

wherein, a heterodyne frequency associated with said Doppler shift is inversely proportional to the wavelength of light being measured, and a reflected amplitude of each wavelength is measured separately by selecting an appropriate heterodyne frequency.

11. The method of claim 9, further comprising the step of:

measuring all the return light with a single detector and using at least one of the spectral amplitude and phase of said reflected light as a continuous function of wavelength in a Fourier transform of a heterodyned signal;

wherein, an absorbancy-versus-wavelength of said sample media is determined by at least one of the spectral amplitude of the reflected light and the phase versus wavelength of the reflected light.

12. The method of claim 9, further comprising the step of:

determining the phase velocity of light versus wavelength of said sample from the spectral phase versus wavelength of the reflected light.

13. The method of claim 9, further comprising the step of:

dividing said return light into the different wavelength components and using optical heterodyning to measure each wavelength on separate detectors.

14. A multiple-frequency spectroscopic quantitation system for measuring light-absorbing species in turbid inhomogeneous medium, the system comprising:

a near infrared light source for generating multiple different wavelengths of light such that one wavelength is selected not to be absorbed by a particular one of the individual targeted species and the other wavelength is selected to be strongly absorbed by said particular one of the individual targeted species, and directing both wavelengths of light into a light beam;

a beam splitter and recombiner for optically splitting said light beam into a sample beam and a reference beam;

a first single mode fiber for passing said sample beam through a sample comprising a turbid inhomogeneous medium that is host to a plurality of said individual targeted species;

a first lens for optically collecting said sample beam affected by said highly diffuse inhomogeneous medium into a reflected sample beam;

a second single mode fiber for reflecting said reference beam on a variable distance mirror with a highly reflective surface;

a second lens for optically collecting reflections of said reference beam from said mirror into a reflected reference beam;

means for optically mixing said affected sample beam and said reflected reference beam, wherein those photons in the reflected sample beam that are within a coherence length of having traveled the same distance in their respective pathlengths with those photons in the reflected reference beam provide for interference fringes for each of said multiple different wavelengths of light that have an amplitude proportional to the number of selected photons in the reflected sample beam;

a photodetector and demodulator for detecting and demodulating the amplitudes of said interference fringes for each of said multiple different wavelengths of light and providing an electric signal proportional to each of said interference fringe amplitudes; and a microcomputer connected with an analog to digital converter to the photodetector and demodulator for ratioing said proportional electrical signals and relating a ratio derived therefrom to a concentration of said individual targeted species in said turbid inhomogeneous medium.

15. The method of claim 14, further comprising the step of:

means for Doppler shifting at least one of the sample beam and reference beam to introduce beating of the reference and sample signals and thus allow for optical heterodyne detection.

16. The method of claim 14, wherein said multiple different wavelength comprises two wavelengths, $\lambda_1$ and $\lambda_2$.

* * * * *